United States Patent [19]

Baniel et al.

[11] Patent Number: 5,231,225
[45] Date of Patent: Jul. 27, 1993

[54] CONCURRENT PRODUCTION OF CITRIC ACID AND ALKALI CITRATES

[75] Inventors: Avraham M. Baniel, Jerusalem; Aharon M. Eyal, Kibbutz Ramat Rachel, both of Israel

[73] Assignee: Innova S.A., Luxembourg, Luxembourg

[21] Appl. No.: 946,169

[22] Filed: Sep. 17, 1992

Related U.S. Application Data

[63] Continuation of Ser. No. 774,154, Oct. 15, 1991, abandoned, which is a continuation of Ser. No. 448,799, Dec. 11, 1989, abandoned.

[51] Int. Cl.$^5$ .................. C07C 51/42; C07C 59/265
[52] U.S. Cl. ................. 562/513; 562/580; 562/584
[58] Field of Search .................. 562/513, 580, 584

[56] References Cited

U.S. PATENT DOCUMENTS

| | | | |
|---|---|---|---|
| 3,086,928 | 4/1963 | Schulz | 562/584 |
| 3,944,606 | 3/1976 | Rieger | 562/584 |
| 4,275,234 | 6/1981 | Baniel et al. | 562/584 |

Primary Examiner—José G. Dees
Assistant Examiner—Joseph Conrad, III
Attorney, Agent, or Firm—Foley & Lardner

[57] ABSTRACT

The known liming sulfuric acid process for the recovery of crystalline citric acid from a fermentation broth is modified by subjecting the mother liquor from the crystallization to extraction with a water-immiscible organic extraction that contains an amine. The resulting extract is neutralized with a recycled brine with alkali citrate and alkali citrate is crystallized from the concentrated brine obtained this way.

12 Claims, 3 Drawing Sheets

CONCURRENT PRODUCTION OF CITRIC ACID AND ALKALI CITRATES

This application is a continuation of application Ser. No. 07/774,154, filed Oct. 15,1991, which is a continuation of application Ser. No. 07/448,799, filed Dec. 11, 1989, both now abandoned.

FIELD OF THE INVENTION

The present invention is in the field of citric acid production and is directed at an improvement in the recovery of citric acid values from citric acid fermentation broths in the form of free citric acid and alkali or ammonium citrate salts.

BACKGROUND OF THE INVENTION AND PRIOR ART

Citric acid is produced commercially by fermentation of carbohydrates and the most common source for carbohydrates for such fermentation are beet molasses. It is also known to use glucose or refined sucrose for the fermentation but, while technically this gives very satisfactory results, it has the drawback of being a costlier primary fermentation feed.

For the recovery of citric acid from a fermentation broth it is possible to use either of two types of technologies. In accordance with the first of these, to be referred to herein as the "lime/sulfuric acid process", the fermentation broth is first subjected to so-called "liming", i.e. treatment with calcium hydroxide, the resulting calcium citrate is filtered off, washed, decomposed with aqueous sulfuric acid, the calcium sulfate that forms is filtered off and the resulting aqueous acidic solution is gradually evaporated in a crystallizer whereupon citric acid crystallizes. If desired, the solution of citric acid obtained by decomposition of the calcium citrate with sulfuric acid may be treated with a variety of ion exchangers and adsorbents in order to remove various impurities prior to crystallization.

Citric acid crystals precipitating in the crystallizer tend to be pure and therefore impurities not removed prior to crystallization accumulate in the mother liquor which is saturated and therefore very concentrated in citric acid. Such accumulation of impurities, if not interfered with, inevitably leads to the inclusion of impurities in the crystallizing citric acid and in order to avoid this, crystallization has to be interrupted once a certain concentration of the mother liquor is reached. The then remaining mother liquor, which is enriched in impurities is recycled to the liming operation. Such recycle usually contains 10 to 20% and sometimes even more of the citric acid produced by fermentation, with the consequence that lime and sulfuric acid are consumed in excess over the stoichiometric quantity with respect to the citric acid produced. Furthermore, the recycle also increases the evaporation load on the crystallizer which is due to the withdrawal of citric acid in form of a very concentrated mother liquor and its redilution upon recycle to the much less concentrated starting solution for the crystallization. Consequently the loading of all operations from liming to crystallization on the recycle takes up production capacity which, but for the recycle, could be used for increasing the production of citric acid. Moreover, use of excessive lime and sulfuric acid increases the amount of gypsum that forms in the process and has to be disposed of, which disposal can be quite costly.

These ongoing problems have been known for a long time and there has been a long-felt want for their solution, but so far without success.

The other technology for recovery of citric acid from a fermentation broth to be referred to herein as "direct extraction method", comprises direct extraction with an organic, water-immiscible extractant followed by recovery of citric acid from the extract. Thus, in accordance with U.S. Pat. No. 3,944,606 alkali metal or ammonium citrates are produced directly from a fermentation broth by extraction with a water immiscible organic extractant consisting of a mixture of a secondary or tertiary amine with an organic solvent, and the resulting organic extract is re-extracted with a compound that forms an alkali metal or ammonium salt of citric acid.

U.S. Pat. No. 4,275,234 teaches to extract an aqueous solution of an acid such as a fermentation broth of citric acid with a water-immiscible organic extractant comprising at least one secondary or tertiary amine in which the total number of carbon atoms per molecule is at least 20, dissolved in a water-immiscible, organic, non-polar or polar solvent, and to back extract the resulting organic solvent extract with water at a higher temperature. According to U.S. Pat. No. 4,334,095 a citric acid fermentation broth is extracted with a mixture of a water-immiscible amine and a water-immiscible organic acid dissolved in a suitable water-immiscible solvent, and the resulting extract is back-extracted with water.

The direct extraction method has the drawback that as distinct from citric acid, citrate salts are not extracted from the fermentation broth. Since fermentation broths obtained by fermentation of molasses are as a rule rich with cations the yield of the direct extraction method is, in such a case, rather low. Consequently, as a practical matter, the direct extraction method is useful only where pure carbohydrates are used for fermentation which, however, is not commonly done because of the high costs involved. A further disadvantage of the direct extraction method is the fact that it yields relatively dilute aqueous solutions of citric acid.

It is the object of the present invention to improve the lime/sulfuric acid process for the recovery of citric acid from a fermentation broth so as to decrease the consumption of lime and sulfuric acid and the evaporation load for crystallization and thereby also decrease the amount of gypsum that has to be disposed of, and at the same time increase the capacity of the citric acid recovery from the fermentation broth.

Citrate salts which must satisfy purity requirements as stringent as those of citric acid are conventionally made from crystallized citric acid, crystalline acid being practically the only form of pure citric acid available. This necessarily involves redissolution of the acid. Prior art teaching the production of citrates from citric acid extracted from fermentation broth involves treating large volumes of the dilute broth, which is costly, and (especially for molasses derived fermentation broths) returning the aqueous residue containing unextracted acid and all the impurities to the lime/sulfuric acid process so that the recycle from crystallization is not materially decreased. It is accordingly a further object of the present invention to provide for the complete recovery of citric acid values as pure citrates from small volumes of concentrated mother liquor remaining upon crystallization of citric acid in the liming/sulfuric acid process.

SUMMARY OF THE INVENTION

In the following specification and claims the term "alkali citrate" is meant to cover mono-, di- and tri-basic alkali metal and ammonium salts of citric acid.

In accordance with the invention there is provided an integrated process for the concurrent recovery of citric acid and alkali citrates from a citric acid fermentation broth comprising treating the fermentation broth with calcium hydroxide, separating the so-formed calcium citrate, decomposing the separated calcium citrate with aqueous sulfuric acid to produce calcium sulfate and an aqueous citric acid solution, separating said aqueous citric acid solution and crystallizing citric acid therefrom by gradual evaporation of water and withdrawing a concentrated mother liquor from the crystallization, characterised by:

i) subjecting said concentrated mother liquor from the crystallization to extraction with an extractant comprising at least one organic amine and a liquid hydrocarbon and separating the resulting extract;

ii) subjecting the said resulting extract to neutralization with an aqueous alkali citrate solution whereby said aqueous alkali citrate brine is formed and said extractant is regenerated;

iii) recycling the regenerated extractant to the extraction of said concentrated mother liquor from the crystallization; and iv) processing said aqueous alkali citrate brine for the recovery of alkali citrate therefrom and recycling the resulting depleted alkali citrate brine to said neutralization.

The alkali citrate brine obtained upon neutralization may be a clear solution or a slurry. The processing for the recovery of alkali citrate may comprise cooling, addition of alkali, e.g. gaseous ammonia, and a combination of such operations. If desired, in addition to or in lieu of adding alkali in the course of the processing of the alkali citrate brine, it is possible to add alkali during the neutralization operation.

The organic amine component of the extractant may be a primary, secondary, tertiary or quaternary amine. It should have at least 18 and preferably 24-40 carbon atoms. The liquid hydrocarbon component of the organic solvent mixture is preferably an aliphatic hydrocarbon. If desired, the solvent mixture may also comprise a further, polar, water-immiscible organic compound such as, for example, a saturated alkanol having at least 6 carbon atoms, a typical example being n-octanol. Such further organic compound improves the compatibility of all components of the extractant and enhances the extraction capacity thereof.

The temperature of the mother liquor from the crystallization which is extracted in accordance with the invention is generally between 50° C. and 80° C. and at such temperature it contains, as a rule, over 50% by weight of citric acid. At such a high concentration only a few counter-current stages are required for fully loading the extractant with citric acid. Upon such multistage counter-current extraction, virtually all the citric acid is transferred to the extractant with only negligible amounts of citric acid remaining alongside the impurities in the raffinate that is sent to waste.

An extractant used in accordance with the present invention is practically fully loaded with citric acid when a proportion of one mole of citric acid to one mole of amine is reached. Accordingly, for the performance of the extraction it is necessary to use an amount of extractant which ensures at least one mole of amine per one mole of citric acid. Higher molar ratios of amine to citric acid are possible since an excess of amine does not adversely interfere with the regeneration of the extractant during the neutralization. This contrasts strongly with known processes for recovering citric acid from a fermentation broth by direct extraction with an amine extractant, in which an excess amine lowers the concentration of the citric acid recovered by back-extraction with water and thus inhibits complete recovery.

The pH at which the extract is neutralized with recycled alkali citrate solution depends on the nature of the citrates in the latter, i.e. whether they are mono-, di- or tri-basic. Thus, depending on the composition of the recycled citrate solution the pH may range from about 3.6 for monoalkali citrate to 11 for trialkali citrate. As a rule one stage contact is sufficient for complete neutralization in a pH range of from 3.6 to 7 with most extractant compositions except those that contain quaternary amines which latter are strong bases and should be used only in plants that produce tri-alkali citrates. Extractants containing tertiary amines are suitable for all citrates and are preferred in plants that produce a variety of citrates.

It is thus seen that in accordance with the invention all citric acid values are recovered from the crystallization mother liquor in an additional operation in which an organic extractant and an aqueous alkali citrate solution flow in closed cycles.

The citrates obtained in accordance with the present invention as an addition to the free citric acid obtained in conventional brine/sulfuric acid processes are valuable commercial products that may be used in the food and detergent industries. Thus, the long-felt need for the effective recovery of citric acid values from the mother liquor remaining from the crystallization of citric acid in the liming/sulfuric acid process is solved for the first time in accordance with the invention.

Within the general teachings of the present invention a variety of modifications are possible in order to adapt the process to specific needs. This flexibility and other features of the invention will become apparent from the now following specific description.

DESCRIPTION OF THE DRAWINGS

For better understanding the invention will now be described by way of example and in a non-limiting manner, with reference to the annexed drawings in which.

DESCRIPTION OF SPECIFIC EMBODIMENTS

Figure 1:
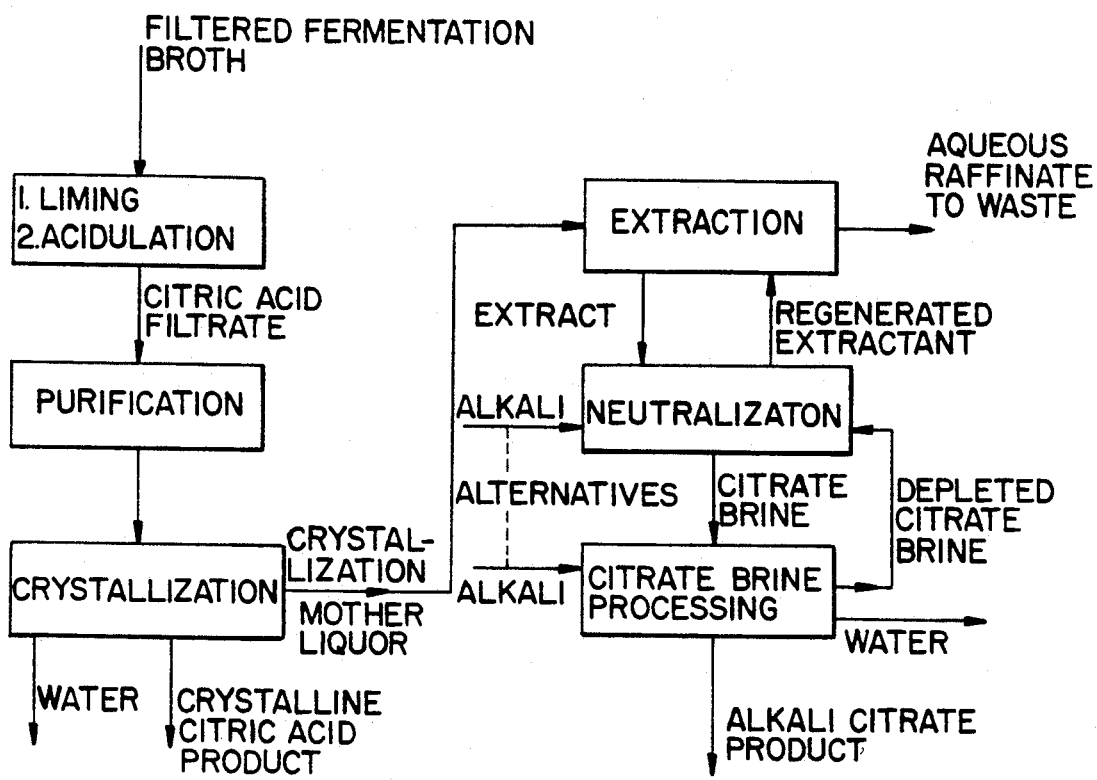
FIG. 1 is a flow diagram of the process according to the invention.

In the flow diagram of FIG. 1, the left-hand side depicts a conventional liming/sulfuric acid process for the recovery of citric acid from a fermentation broth. As shown, the filtered fermentation broth is charged into a liming and acidulation operation, the filtrate from that operation is subjected to purification and the resulting, partly purified solution is charged into a crystallizer where the aqueous solution is gradually concentrated with the formation of crystalline citric acid monohydrate which is withdrawn as product. All these operations are known per se and need not be described in detail.

The additional operations provided in accordance with the invention for the recovery of additional citric acid values from the crystallization filtrates are depicted on the right-hand side of the flow diagram of FIG. 1. As shown, the mother liquor from the crystallization is charged into an extraction operation where it is contacted with recycled extractant of the kind hereinbefore defined. Aqueous raffinate from the extraction operation is withdrawn as waste while the resulting extract is subjected to neutralization with a recycled alkali citrate brine. This neutralization causes the formation of a additional alkali citrate brine and concommitant liberation of extractant which is recycled into the extraction operation. The alkali citrate brine withdrawn from neutralization is charged into a processing unit in which the solution may be evaporated, cooled and an alkali added, precipitated alkali citrate is separated and the remaining depleted brine is recycled to neutralization.

It is thus seen that in accordance with the present invention both crystalline citric acid and crystalline alkali citrate are obtained concurrently as products while the waste is an aqueous raffinate bearing very little citric acid, if any.

Where the concentration of the depleted alkali citrate brine recycled from the processing to the neutralization unit is significantly below saturation, some alkali may be added to the neutralization unit.

As mentioned, the extractant contains preferably some water-immiscible, polar organic compound such as, for example n-octanol which ensures good compatibility of all components in the extractant stream and also enhances the extraction strength of the amine, especially of weak amines.

The flexibility of the process according to the invention is illustrated in Table 1 below. In this table all the extractants in column 1 marked E.1 to E.8 contain one mole of amine per one kg of extractant so that at saturation they contain close to 16% by weight of citric acid (16.12% is the theoretical concentration for an anhydrous extractant loaded with one mole of amine citrate); column 2 identifies the amine; column 3 shows the amount of n-octanol that was added expressed in weight percentage of the extractant; column 4 states the molar ratio of the amine in the extractant to the citric acid in the mother liquor; column 5 indicates the average temperature of extraction which may vary up to 5° C. in both directions; column 6 indicates the number of counter-current liquid-liquid contactings applied in extraction; and column 7 indicates the lowest concentration of citric acid in the aqueous phase that is in equilibrium with an extractant loaded with 0.9 mole of citric acid per one mole of amine.

TABLE 1

| (1) EXTRACTANT | (2) AMINE | (3) OCT. % | (4) RATIO | (5) °C | (6) STAGES | (7) 0.9 SAT. |
|---|---|---|---|---|---|---|
| E1 | tertiary[1] | 5 | 1.1 | 28 | 3 | 1.55 |
| E2 | tertiary[1] | 10 | 1.1 | 28 | 3 | 1.45 |
| E3 | tertiary[1] | 30 | 1.1 | 28 | 2 | 1.38 |
| E4 | tertiary[1] | 10 | 1.1 | 75 | 4 | 1.5 |
| E5 | tertiary[1] | 10 | 1.2 | 75 | 3 | 1.5 |
| E6 | secondary[2] | 5 | 1.1 | 75 | 3 | 1.45 |
| E7 | primary[3] | 5 | 1.05 | 75 | 3 | 1.15 |

TABLE 1-continued

| (1) EXTRACTANT | (2) AMINE | (3) OCT. % | (4) RATIO | (5) °C | (6) STAGES | (7) 0.9 SAT. |
|---|---|---|---|---|---|---|
| E8 | quaternary[4] | 5 | 1.01 | 75 | 2 | <0.1 |

[1] Alamine 304 (Henkel Corp) a technical grade tridodecylamine; equivalent weight averaged 558.
[2] Amberlite-LA1 (Rohm & Haas)**
[3] Primene JM-T (Rohm & Haas), of formula $CH_3(CH_2)_nC(CH_3)_2NH_2$.
[4] Methyl tricaprylyl ammonium hydroxyde obtained by washing the corresponding chloride (Aliquat 336, Henkel Corp.) with NaOH.

Columns 4 to 7 in the above Table 1 describe experimental extractions according to the basic flow diagram of FIG. 1 in which over 99% by weight of citric acid was recovered from a mother liquor that contained 50% by weight of citric acid.

Figure 2:
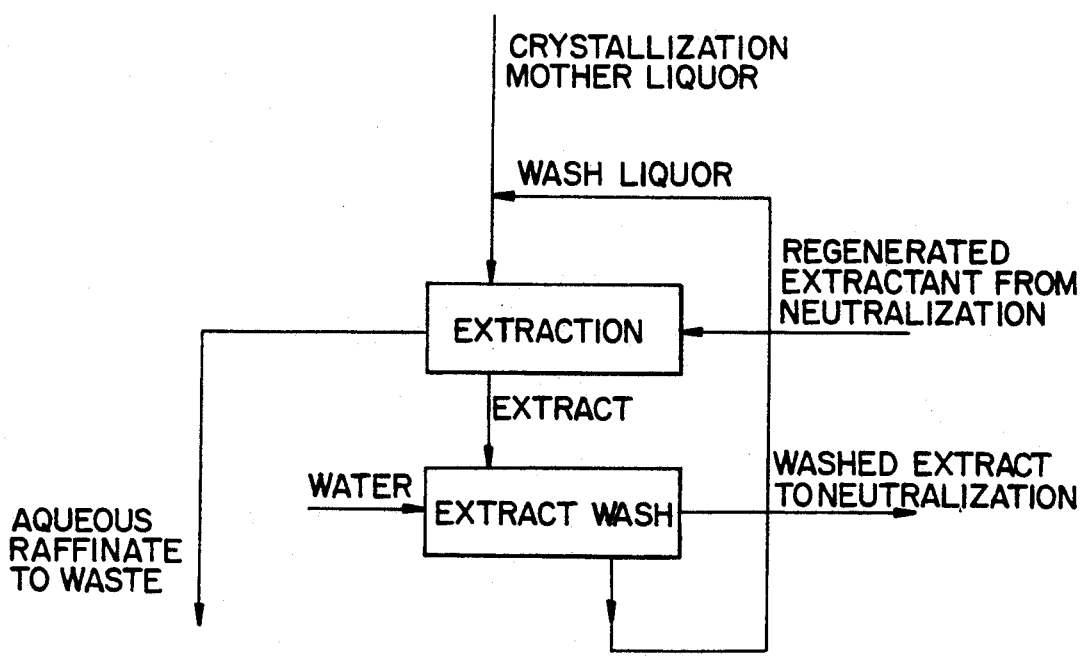
FIG. 2 is a fractional flow diagram of a modification of a process of FIG. 1.

In industrial practice it is desirable to interpose between extraction and neutralization a washing operation in which the extract is contacted with water to complete the removal of impurities that may be dissolved in the extract or be dispersed therein as fine droplets of aqueous phase. Such a modification is depicted in FIG. 2 where, as shown, the aqueous phase resulting from such wash and which contains citric acid, is recycled to the mother liquor feed. The dilution caused by the recycled wash does not affect materially the extraction.

Figure 3:
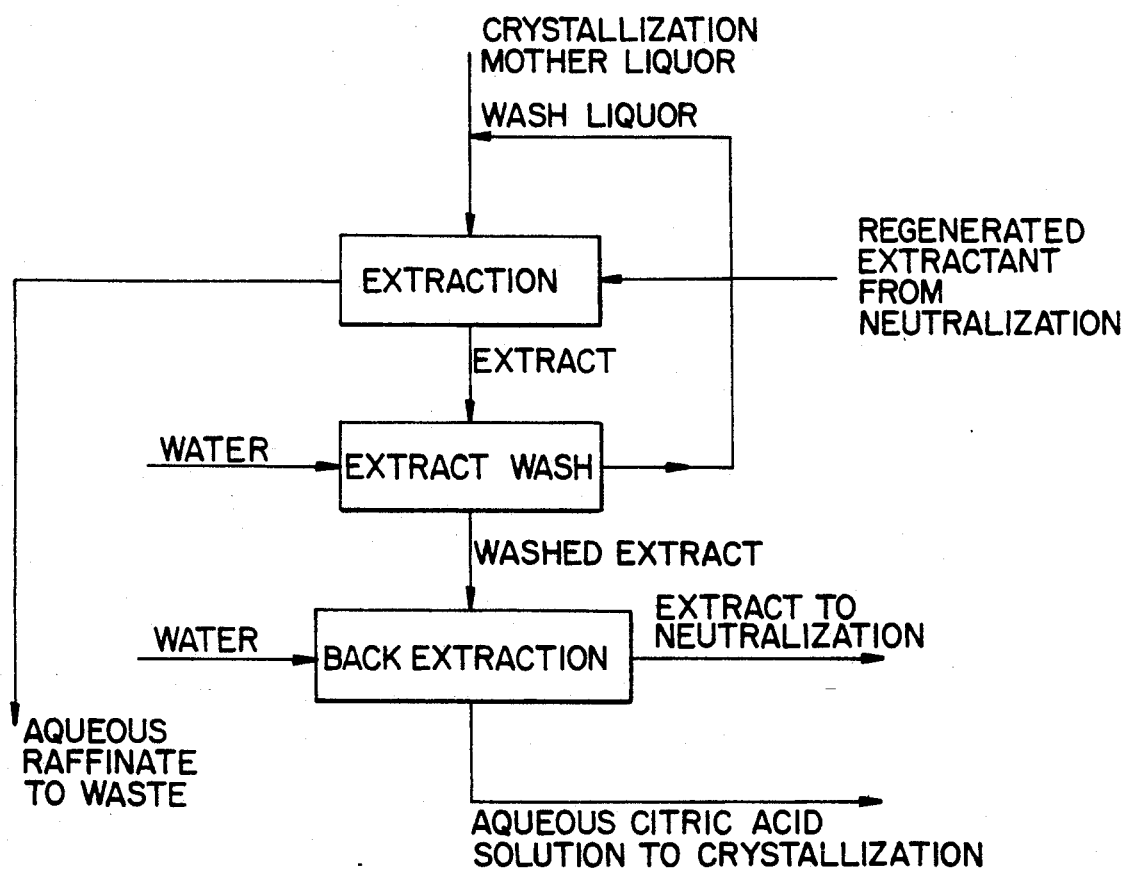
FIG. 3 is a fractional flow diagram of another modification.

The amount of mother liquor available in the production of citric acid may exceed the amount that can be accepted for the production of alkali citrate. In such a case it would be necessary to recycle part of the mother liquor to liming in the conventional manner. However, within limits, such a recycle can be avoided by back-extracting the wash extract with water prior to neutralization and charging the resulting aqueous extract into the crystallizer. Such a modification is shown in FIG. 3.

The possibilities and limitations of citric acid recycle can be gauged from the following Table 2 which illustrates the effect of contacting a fully loaded extractant of composition E2 in Table 1 with varying amounts of water. In Table 2 CA stands for citric acid.

TABLE 2

| | CA RECYCLE | |
|---|---|---|
| H₂O WT % | CA in CA RECYCLE | |
| ON EXTRACT* | CONCENTRATION WT % | % OF TOTAL |
| 14.6 | 20 | 17.3 |
| 23.7 | 16 | 22.3 |
| 57.6 | 10 | 33.9 |
| 84.7 | 8 | 39.9 |

*Extract Extractant E2 loaded with 16.1 wt. % citric acid

The following Table 3 shows the percentage of citric acid that can be recycled in accordance with FIG. 3 in the operations described in Table 1, without undue dilution.

TABLE 3

| Extractant | % Recycle |
|---|---|
| E1 | 15 |
| E2 | 20 |
| E3 | 15 |
| E4 | 20 |
| E5 | 15 |
| E6 | 15 |
| E7 | 10 |
| E8 | <1 |

It follows from Table 3 that with certain tertiary amines up to 20% by weight of the acid extracted from the mother liquor can be recycled to crystallization without incurring excessive dilution and this provides for useful adjustments in the manufacture of alkali citrates from the mother liquor.

By reading together Tables 1 and 3, it follows that while all four varieties of amines may be used in devising extractants suitable for the purpose of the present invention, quaternary amines do not admit recycle and primary amines provide for less recycle than secondary and tertiary amines. In general, extractant characteristics can be most readily manipulated with tertiary amines. They are therefore preferred in the practice of the present invention. In particular extractants composed of tridodecylamine, n-octanol and a $C_{10}$–$C_{11}$ isoparaffin diluent, as illustrated by compositions E1 to E5 in Table 1 are preferred since they also fall within the Code of Federal Regulations, Title 21 (173,280 published by the U.S. Government Printing Office, Washington DC, 1977) that allows these compositions to be used in preparing food grade citric acid.

The temperature of extraction is not critical. If allowed to establish itself without interference, it will be in a range determined by the temperature of the mother liquor, the heating effect of neutralization, the temperature of recycled citrate brine, the cooling effect of water added to the extract wash and citric acid recycle in accordance with the embodiments of FIGS. 2 and 3, and heat losses to the environment. As a rule the temperature of extraction will be within the range of 30° to 90° C. and in most cases within the range of 40° to 80° C. Thus, by comparing the results in experiments E1–E5 in Table 1 with each other, it is seen that the extraction efficiency is not significantly varied within the temperature range of 28°–75° C. which means that there is in fact no need for any regulation of temperature. This contributes to the simplicity of the implementation of the present invention and to savings in equipment and energy.

Citric acid carried in the extract cannot be reacted with alkali as if it were in water solution. If the alkali is anhydrous, e.g. ammonia gas or solid sodium hydroxide, strong exothermic reactions take place at the point of alkali introduction leading rapidly to unmanageable mixtures. With $NH_3$ the ammonium citrate resulting from the initial reaction is in the form of fine crystals which rapidly form a thick suspension in which little further reaction takes place upon continuation of the pumping through of $NH_3$. Solid NaOH is instantaneously coated with insoluble sodium citrate that prevents a further reaction. If the common commercial form of 50% solution of NaOH is used, the heat evolved at the point of contact of the alkali with the extractant may chemically damage extraction components and the aqueous phase containing fine crystals tends to emulsify into a thick unmanageable mass.

It is known from the prior art to neutralise a citric acid organic extract with alkali in an equivalent amount to the citric acid it carries when this alkali is dissolved in an amount of water sufficient to hold in solution the citrate that is formed and which is subsequently recovered by evaporation of the water to obtain the crystalline citrate. It is against the background of this knowledge that in the practice of the present invention the formation of viscous masses as well as forced introduction of $H_2O$ that must subsequently be eliminated are totally avoided by the device of using for the neutralization a recycled saturated or nearly saturated alkali citrate brine. This recycled brine does not introduce fresh water into the system and the proportion of the aqueous phase to the solvent phase can be set to maximise the operational effectiveness. Generally this proportion will be in the range of aqueous volume ratios of from 0.2:1 to 10:1, the range of 0.5:1 to 3:1 having been found to be satisfactory in most cases. Within these proportions the phases equilibrate on mixing and separate smoothly and allow for fine control of neutralization and crystallization of citrates in ways specifically adjusted to every citrate as explained and illustrated in the examples below.

Figure 4:
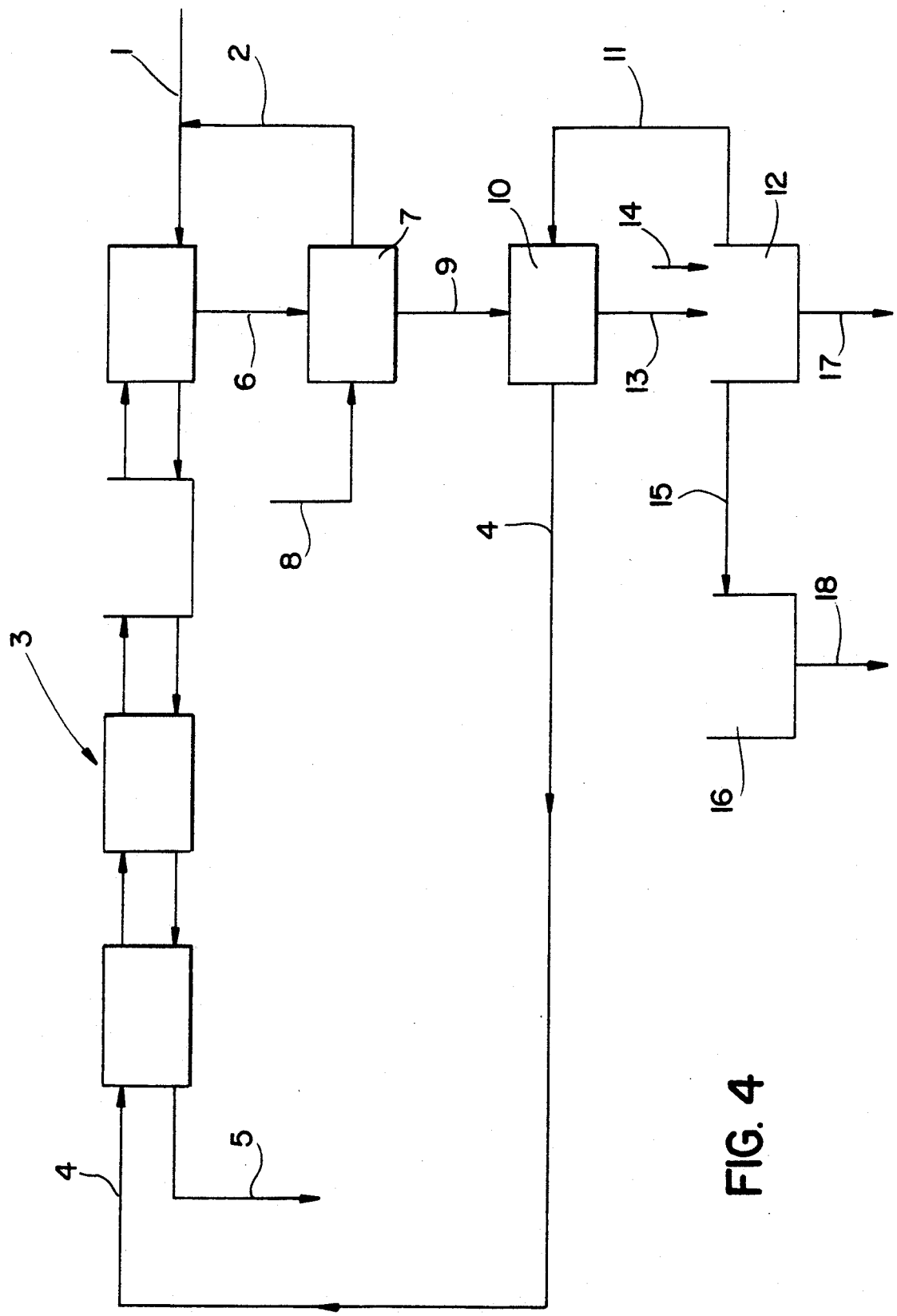
FIG. 4 is a flow diagram of a specific example.

FIG. 4 is a flow diagram of a specific process according to the invention and will be described in Example 5 below.

The invention is now further illustrated by the following examples:

EXAMPLE 1

An extract consisting of an extractant of composition E1 in Table 1 carrying 1 mol of citric acid per 1 Kg of extractant (which approximates 0.7 mol/L) and at a temperature of about 45° C., is mixed with a solution of dibasic ammonium citrate $(NH_4)_2HC_6H_5O_7$ recycled from a crystallizer operated at 40° C. (and therefore saturated when at 40° C.) in a proportion of 3:1 extract to aqueous. Neutralisation occurs very rapidly, part of the dibasic citrate which is present in large excess being converted into the monobasic citrate:

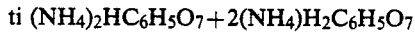
ti $(NH_4)_2HC_6H_5O_7 + 2(NH_4)H_2C_6H_5O_7$

The pH of the aqueous phase approximates 4.2 which ensures complete release of extractant E1. One minute residence time in a baffled cylindrical turbine mixer of standard design was found sufficient. The mixture that has a temperature of about 43° C. settles easily into a clear extractant phase that is recycled to the process and a clear aqueous phase that is further processed as follows: it is sent to a mixer in which it is ammoniated by means of gaseous ammonia so as to convert the monobasic citrate in the solution to the dibasic citrate

$(NH_4)H_2C_6H_5O_7 + NH_3 \rightarrow (NH_4)_2HC_6H_5O_7$ and reform a solution containing only the dibasic salt; on cooling to 40° C. in a crystallizer, dibasic citrate in an amount equivalent to the citric acid present in the extract crystallizes and is collected as product; the mother liquor is recycled to neutralization and thereby the cycle is completed.

A noteworthy aspect of this process is that virtually no water need be evaporated since none is purposefully introduced. A small amount may enter the citrate brine through the extractant but is easily eliminated when vacuum is applied in the crystallizer. In contrast, when crystalline citric acid is used for the production of ammonium citrate, it must be dissolved prior to ammoniation and this amount of water—roughly of equal weight to the citric acid ammoniated—must subsequently be eliminated.

EXAMPLE 2

Extractant and recycle brine are the same as in Example 1 and are used in the same proportions but the recycle brine is ammoniated by $NH_3$ gas prior to contacting the extract. The ammonia dissolves in the brine converting part of the dibasic citrate to tribasic citrate $$(NH_4)_2HC_6H_5O_7 + NH_3 \rightarrow (NH_4)_3C_6H_5O_7$$

The ammoniated brine which has a pH of about 5.7 effects the neutralization of the extract and the mixture is processed as in the previous example.

EXAMPLE 3

Materials and proportions are as in Example 2. However, the crystalline product citrate is obtained directly upon neutralization by controlling the temperature. This is achieved most conveniently by cooling the extract, prior to contacting, sufficiently (in the present case to about 29° C.) to absorb the heat of reaction so as to establish upon admixture of the recycled citrate brine a temperature approximately equal to the chosen crystallization temperature such as 40° C. The crystalline product is separated together with the aqueous phase by which it is wetted, then filtered or centrifuged.

EXAMPLE 4

The operation is in accordance with FIG. 1, all percentages indicating composition being by weight. A recycle brine containing trisodium citrate 30%, disodium citrate 10% and water 60% and having a temperature of 50° C. is mixed with a 50% caustic soda (NaOH) solution at a ratio of 160 grs per 1 Kg brine whereupon a homogenous aqueous solution is formed of approximately pH 8. An extract at 50° C. or higher obtained by extraction of mother liquor by an extractant of composition E3 in Table 1 is neutralized by this aqueous solution in proportions such that the added alkali corresponds to the citric acid in the extract. On phase separation an extractant free of citric acid is obtained and a citrate brine that is subjected to evaporation to remove the water added with the alkali and cooling to 50° C. (both operations being concurrently effected in a crystallizer) whereby an anhydrous crystalline disodium citrate is recovered.

EXAMPLE 5

Citric acid (CA) is produced in the conventional liming/sulfuric acid process. Mother liquor is formed at the rate of 250 gr per 1000 gr product. 26.6 gr/min of this mother liquor containing 73% CA is fed at 1 concurrently with wash solution recycled at 2, into a four-stage counter-current extractor 3. Extraction is effected with 120 gr/min regenerated extractant introduced at 4 and composed of 558 gr/kg triburyl amine (Alamine 304 by Henkel), 100 gr/kg octanol and 342 gr/kg aliphatic hydrocarbons mixture (Norpar 12 by Exxon). 9.5 gr/min of an aqueous raffinate containing 2.1% CA (which corresponds to less than 1% of the CA contained in the mother liquor subjected to extraction) is withdrawn at 5 and discarded. A loaded organic phase is withdrawn from the extraction at 6 and is washed in a one stage liquid-liquid contactor 7 with 5 gr/min deionized water introduced at 8 to yield a wash solution which is withdrawn at 2 and recycled, and 142 gr/min of an organic phase withdrawn at 9. This organic phase is contacted in a one stage liquid-liquid contactor 10 with 430 gr/min depleted alkali citrate brine arriving at 11 from a trisodium citrate (TSC) crystallizer 12, to regenerate the extractant which is recycled at 4 and to form a sodium citrate brine which is withdrawn at 13. This sodium citrate brine is fed to the crystallizer 12 together with 24 gr/min of a 50% NaOH solution introduced at 14. 16 gr/min water is evaporated in crystallizer 12, the vapour is withdrawn at 15 into a condenser 16 and condensed water is withdrawn at 18. 294 gr/min TSC precipitate is withdrawn from crystallizer 12 at 17 and 430 gr/min mother liquor is recycled at 11 to the neutralization operation in contacter 10. Analysis of the TSC product for readily carbonisable substances show contents lower than those in TSC obtained by direct neutralization of CA of F.C.C. specification by sodium hydroxide.

The foregoing examples illustrate that making citrates according to the present invention by neutralization of an extract with a recycle alkali citrate brine close to saturation provides for great latitude in selecting optimal conditions for the desired alkali citrate production in terms of temperature of crystallization, freedom in selecting crystallizers that operate on an aqueous solution and the possibility of by-passing or greatly decreasing the need for a separate crystallization operation by creating conditions to harvest crystals in neutralization. Further, evaporation demands are reduced to a minimum viz., to the amount of water added with the alkali and some water that accompanies the citric acid in the extract.

Referring again to FIG. 1, an extraction section of this process can fit a variety of citrates and a suitable extractant may be selected in accordance with the teachings of this invention. The alkali citrate section may produce several citrates if properly equipped, in accordance with commerical requirements.

We claim:

1. In an integrated process for the concurrent recovery of citric acid and alkali citrate from a citric acid fermentation broth comprising treating the fermentation broth with calcium hydroxide, separating the so-formed calcium citrate, decomposing the separated calcium citrate with aqueous sulfuric acid to produce calcium sulfate and an aqueous citric acid solution, separating said aqueous citric acid solution and crystallizating citric acid therefrom by gradual evaporation of water and withdrawing a concentration mother liquor from the crystallization, the improvement by which alkali citrate is recovered from said concentrated mother liquor by:
   i) subjecting said concentrated mother liquor from the crystallization to extraction with an extractant comprising at least one organic amine and a liquid hydrocarbon and separating the resulting extract;
   ii) subjecting the said resulting extract to neutralization with an aqueous alkali citrate solution whereby said aqueous alkali citrate brine is formed and said extractant is regenerated;
   iii) recycling the regenerated extractant to the extraction of said concentrated mother liquor from the crystallization; and
   iv) processing said aqueous alkali citrate brine for the recovery of alkali citrate therefrom and recycling the resulting depleted alkali citrate brine to said neutralization.

2. A process according to claim 1, wherein said at least one organic amine of the extractant is a tertiary amine having at least 18 carbon atoms.

3. A process according to claim 2, wherein said tertiary amine has 24 to 40 carbon atoms.

4. A process according to claim 3, wherein said tertiary amine is tridodecylamine.

5. A process according to claim 1, wherein said extractant further comprises a saturated alkanol having at least 6 carbon atoms.

6. A process according to claim 1, comprising washing said resulting extract containing citric acid, from step (i), with water, and then subjecting the washed extract to said neutralization in step (ii), the aqueous wash liquor from said washing being recycled to the mother liquor feed to the extraction.

7. A process according to claim 6, comprising subjecting said washed extract to back extraction with water to produce an aqueous citric acid solution and recovering crystalline citric acid therefrom, the depleted extract then being subjected to neutralization in step (ii).

8. A process according to claim 1, wherein the processing of said alkali citrate brine comprises cooling.

9. A process according to claim 1, wherein the processing of said alkali citrate brine comprises the addition of alkali.

10. A process according to claim 1, wherein alkali is added during neutralization.

11. A process according to claim 1, wherein in step (i), the extraction is effected at a temperature of 30°-90° C.

12. A process according to claim 11, wherein the extraction is effected at a temperature of 40°-80° C.

* * * * *